United States Patent
Bartholomäus et al.

(10) Patent No.: US 6,875,447 B2
(45) Date of Patent: Apr. 5, 2005

(54) PARENTERAL DOSAGE FORMS COMPRISING A SUSPENSION OF TRAMADOL SALT AND DICLOFENAC SALT

(75) Inventors: Johannes Bartholomäus, Aachen (DE); Heinrich Kugelmann, Aachen (DE)

(73) Assignee: Grunenthal GmbH, Aachen (DE)

( * ) Notice: Subject to any disclaimer, the term of this patent is extended or adjusted under 35 U.S.C. 154(b) by 0 days.

(21) Appl. No.: 10/442,701

(22) Filed: May 21, 2003

(65) Prior Publication Data

US 2003/0203037 A1 Oct. 30, 2003

Related U.S. Application Data

(63) Continuation of application No. PCT/EP01/13789, filed on Nov. 27, 2001.

(51) Int. Cl.$^7$ .......................... A61K 31/60; A61K 31/42
(52) U.S. Cl. ........................................ 424/464; 424/489
(58) Field of Search ................. 424/400, 422, 424/484, 489

(56) References Cited

U.S. PATENT DOCUMENTS

| | | | |
|---|---|---|---|
| 4,016,273 A | 4/1977 | Sieger et al. ............... | 424/250 |
| 4,614,741 A * | 9/1986 | Dell et al. ................ | 514/226.5 |
| 5,283,067 A * | 2/1994 | Geller et al. ................ | 424/489 |
| 5,336,691 A | 8/1994 | Raffa et al. .................. | 514/629 |
| 5,665,394 A * | 9/1997 | Igari et al. .................. | 424/501 |
| 5,958,379 A | 9/1999 | Regenold et al. ............. | 424/47 |

FOREIGN PATENT DOCUMENTS

| | | | | |
|---|---|---|---|---|
| DE | 19732928 A1 | 2/1999 | | |
| EP | 0546676 A1 * | 6/1993 | .......... | A61K/31/60 |
| WO | WO 98/50075 | 11/1998 | | |
| WO | WO 00/29022 | 5/2000 | | |
| WO | WO 00/29023 | 5/2000 | | |
| WO | WO 00/72827 A2 | 12/2000 | | |

OTHER PUBLICATIONS

"Multicenter Trial Comparing Tramadol And Morphine For Pain After Abdominal Surgery", Gritti et al., Drugs Explt. Clin. Res XX1V (1) 9–16, 1998.
"Computer–controlled Drug Release From Small–sized Dosage Forms", R. Groning, Journal of Controlled Release 48, 185–193, 1997.

* cited by examiner

Primary Examiner—Thurman K. Page
Assistant Examiner—Sharon Howard
(74) Attorney, Agent, or Firm—Perman & Green, LLP.

(57) ABSTRACT

The invention relates to parenteral dosage forms of administration that comprise a suspension of the salt of the active substances tramadol and diclofenac.

29 Claims, 2 Drawing Sheets

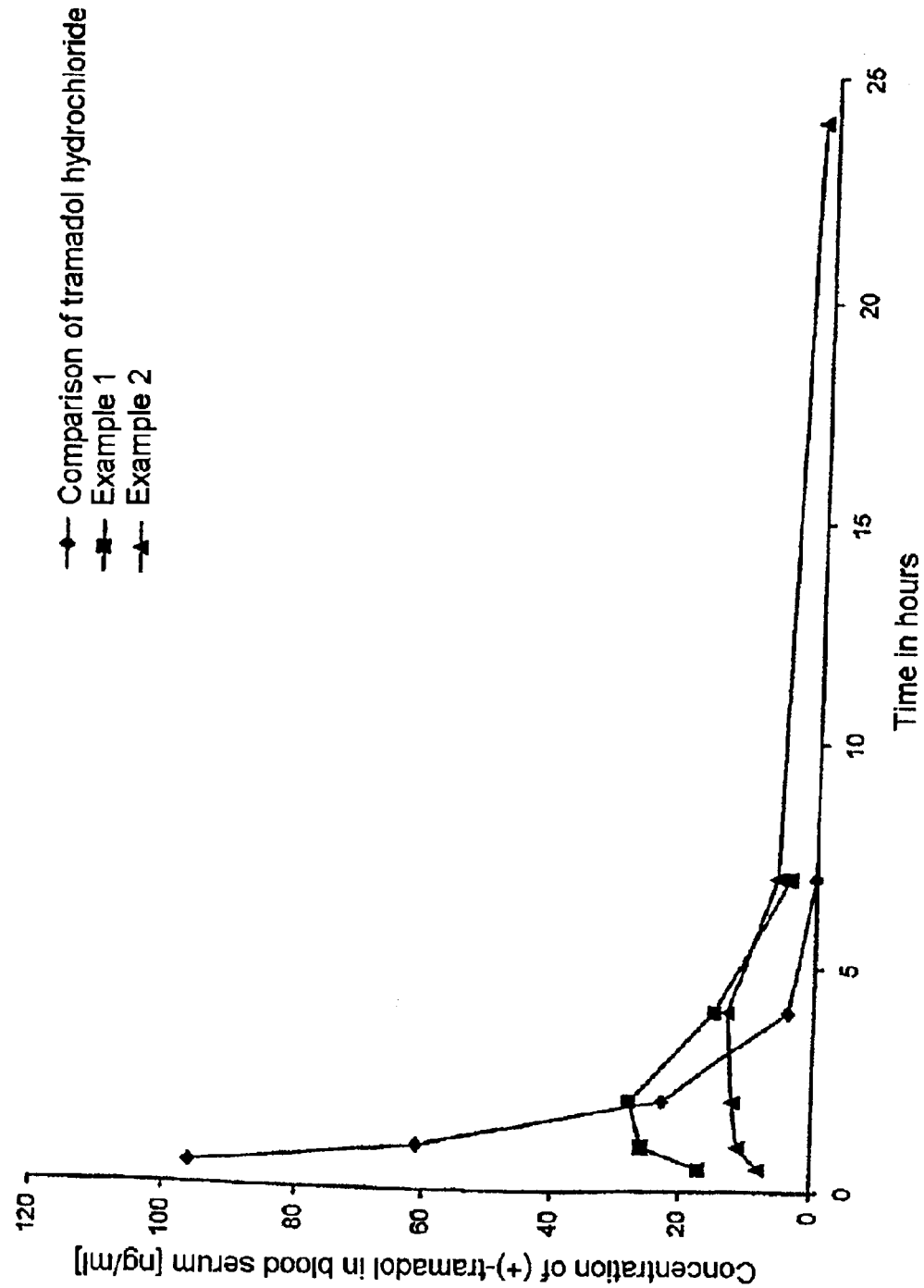

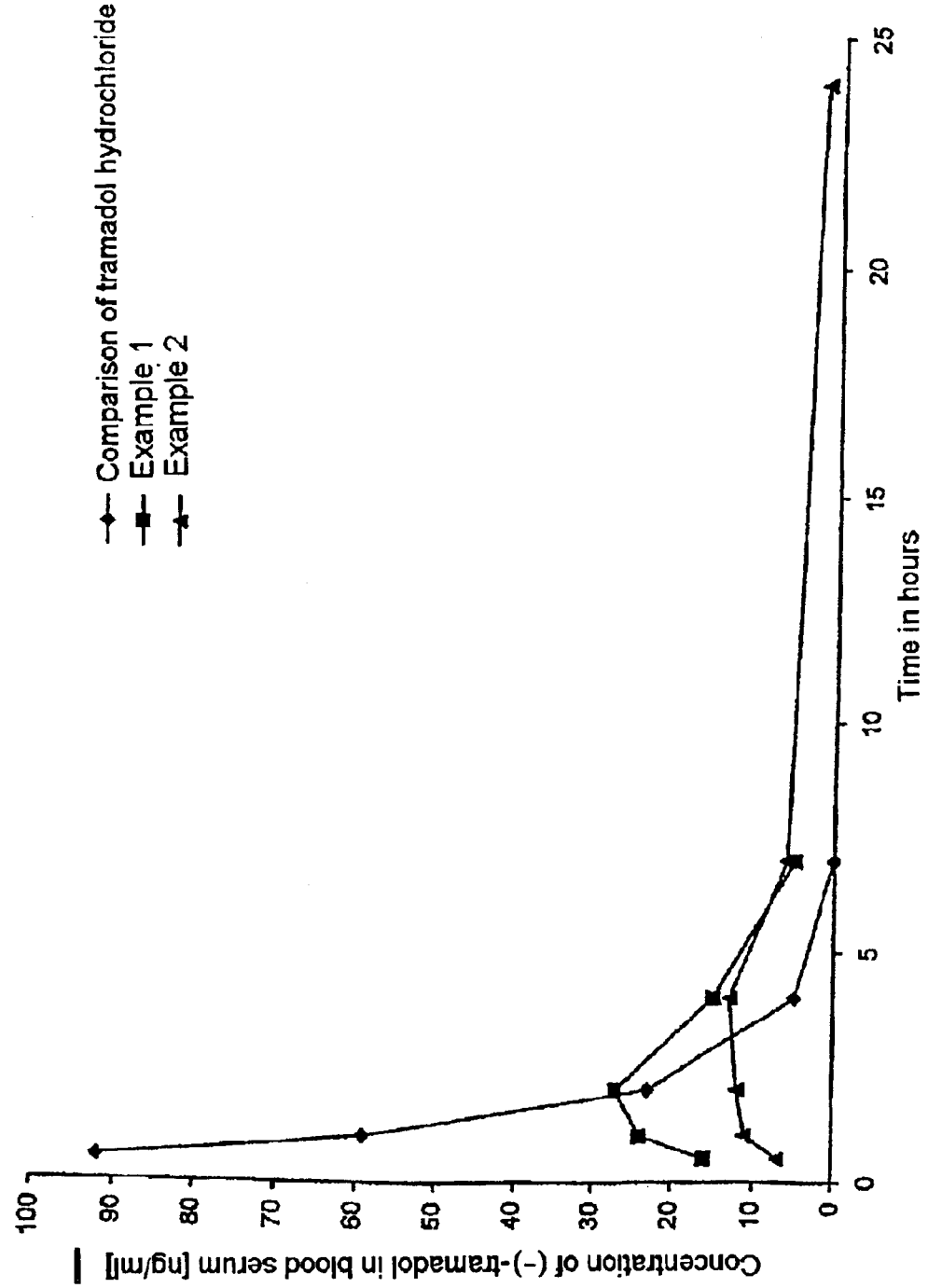

PARENTERAL DOSAGE FORMS COMPRISING A SUSPENSION OF TRAMADOL SALT AND DICLOFENAC SALT

This application is a continuation of international application number PCT/EP01/13789 filed Nov. 27, 2001, status pending.

The present invention relates to dosage forms which can be administered parenterally and comprise a suspension of the salt of the active ingredients tramadol and diclofenac.

The active pharmaceutical ingredient tramadol is frequently employed in the form of its hydrochloride—(1RS, 2RS)-2-[(dimethylamino)methyl]-1-(3-methoxy-phenyl) cyclohexanol hydrochloride—as analgesic for controlling moderate to severe pain.

Satisfactory control of pain in some patients is possible only by parenteral administration of the analgesics, for example if the patient is unable or only poorly able, because of his physical incapacity, to take an analgesic orally.

One disadvantage of parenteral administration of tramadol hydrochloride is the relatively rapid metabolism of the active ingredient from dosage forms known to date, so that a longer-lasting analgesic effect cannot be achieved after its administration without increasing the dosage. However, such an increase is undesirable because the risk of unwanted side effects is also increased thereby.

The object on which the present invention was based was therefore to provide a dosage form of the active ingredient tramadol for parenteral administration from which metabolism of this active ingredient is retarded.

This object is achieved according to the invention by the provision of dosage forms which can be administered parenterally and which comprise a suspension of the salt of the active ingredients tramadol and diclofenac.

The salt of the active ingredients tramadol and diclofenac is preferably prepared by reacting a very water-soluble salt of tramadol with a very water-soluble salt of diclofenac. The tramadol salt preferably employed is tramadol hydrochloride, and the diclofenac salt preferably employed is its sodium salt. The salt of the active ingredients tramadol and diclofenac obtained in this way can be isolated and, where appropriate, purified by various methods known to the skilled worker.

In a preferred embodiment of the present invention, at least 95% of the suspended salt particles of the novel dosage forms which can be administered parenterally have a particle diameter in the range $\leq 50$ μm, preferably $\leq 30$ μm, particularly preferably $\leq 5$ μm.

The particle diameters of the suspended salt particles are determined by scattered light measurement in a Coulter® LS 230 laser particle analyzer with HFM and MVM modules (Beckman-Coulter Electronis GmbH, Krefeld, Germany).

The suspending medium of the novel dosage forms which can be administered parenterally may be hydrophobic or hydrophilic.

One embodiment of the present invention therefore comprises suspending the salt of the active ingredients tramadol and diclofenac in a hydrophobic pharmaceutically acceptable suspending medium. This hydrophobic suspending medium may preferably be based on pharmaceutically acceptable synthetic, semisynthetic or natural oils or mixtures of at least two of these oils.

Synthetic, semisynthetic or natural oils which can preferably be employed are medium chain length triglycerides with a chain length of from $C_8$ to $C_{10}$ in the carboxylic acid moiety, soybean oil, sesame oil, peanut oil, olive oil, coconut oil, castor oil, sunflower oil, safflower oil or the corresponding hydrogenated oils or mixtures of at least two of the aforementioned oils. Castor oil is particularly preferably employed. It is also possible where appropriate for these oils to be furnished with physiologically tolerated antioxidants, preferably tocopherols and/or esters thereof, butylated hydroxyanisole or butylated hydroxytoluene, preferably in amounts of from 0.001 to 0.1% by weight based on the suspending medium.

It is also possible to employ for the novel dosage forms which can be administered parenterally of the active ingredient salt a physiologically tolerated hydrophilic suspending medium. The hydrophilic suspending medium is preferably based on water.

The physiologically tolerated hydrophilic suspending medium may, besides water, comprise other physiologically tolerated excipients. These excipients are preferably pH regulators, regulators to adjust the osmolality, surface-active compounds, viscosity regulators, peptizers, buffers or preservatives.

Besides one or more regulators to adjust the osmolality, the novel dosage forms may further comprise one or more representatives of one to all of the other classes of excipients mentioned.

If the dosage forms of the invention which can be administered parenterally comprise physiologically tolerated surface-active compounds, those preferably employed are polyalkylene glycols such as polyethylene glycols, polypropylene glycols or ethylene oxide, propylene oxide block copolymers, phospholipids, ethers or esters of saturated or unsaturated fatty alcohols or fatty acids with polyalkylene glycols such as polyethylene glycols or polypropylene glycols, polysorbates such as mono-, di- or triesters of saturated or unsaturated fatty acids, particularly preferably oleic acid, lauric acid, palmitic acid or stearic acid, and sorbitol and/or its anhydride, each of which may have up to 20 mol of ethylene oxide units per mole of sorbitol or anhydride, preferably polyethoxysorbitan monolaurate with 20 ethylene oxide units, polyethoxysorbitan monolaurate with 4 ethylene oxide units, polyethoxysorbitan monopalmitate with 20 ethylene oxide units, polyethoxysorbitan monostearate with 20 ethylene oxide units, polyethoxysorbitan monostearate with 4 ethylene oxide units, polyethoxysorbitan tristearate with 20 ethylene oxide units, polyethoxysorbitan monooleate with 20 ethylene oxide units, polyethoxysorbitan monooleate with 5 ethylene oxide units or polyethoxysorbitan trioleate with 20 ethylene oxide units, or a mixture of at least two of the aforementioned surface-active compounds.

A large number of the corresponding polysorbates is marketed under the proprietary name Tween® by the UNIQEMA/ICI group of companies.

In order to minimize or completely eliminate the risk of cell and tissue damage, the osmolality, i.e. the tonicity of the dosage forms of the invention which are to be administered parenterally, is preferably adjusted so that they are isotonic or at least approximately isotonic to the physiological osmolality. The osmolality of the dosage forms of the invention which can be administered parenterally is therefore preferably adjusted so that it is in the range from 250 to 400 mOsm/kg, particularly preferably in the range from 260 to 320 mOsm/kg and very particularly preferably in the range from 280 to 300 mOsm/kg.

Preferred regulators for adjusting the osmolality are water-soluble, physiologically tolerated compounds such as inorganic salts, e.g. alkali metal salts, preferably sodium chloride, sugars, e.g. sucrose or dextrose, sugar alcohols, e.g. mannitol, or polyalkylene glycols, e.g. polyethylene glycols, preferably having a molecular weight of from 1 000 to 8 000 g/mol. It is also possible to use a mixture of at least two representatives of different aforementioned classes of regulators or at least two representatives of one class of regulators for adjusting the osmolality.

It is also possible where appropriate to employ a regulator to adjust different properties of the dosage forms of the invention. For example, a surface-active compound can also be used to adjust the osmolality.

The pH of the dosage forms of the invention should preferably be in the range from pH 5 to pH 8 in order to avoid further risks of cell and tissue damage.

The dosage forms of the invention which can be administered parenterally may also comprise physiologically tolerated preservatives. Examples of such which are suitable are 1,1,1-trichloro-2-methyl-2-propanol, phenylethyl alcohol, sorbic acid, benzyl alcohol, alkylbenzyldimethylammonium chloride with a chain length of from $C_8$ to $C_{18}$ in the alkyl moiety, m-cresol or alkyl-4-hydroxybenzoate, preferably methyl-4-hydroxybenzoate or propyl-4-hydroxybenzoate. It is also possible to employ mixtures of two or more of the aforementioned preservatives.

In a particularly preferred embodiment of the present invention, the suspending medium of the dosage forms of the invention is water, which comprises as further excipients
  a) 0.001 to 1% by weight, preferably 0.0015 to 0.1% by weight, particularly preferably 0.005 to 0.015% by weight, of physiologically tolerated surface-active compounds, preferably polysorbates, particularly preferably sorbitol and/or its anhydrides which are monoesterified with oleic acid, lauric acid, palmitic acid or stearic acid and esterified with polyethylene glycol, preferably with polyethylene glycol having a molecular weight of from 1 000 to 8 000 g/mol
  b1) 3 to 10% by weight of at least one osmolality regulator selected from the group of monosaccharides, oligosaccharides and sugar alcohols, preferably sucrose and/or mannitol, or
  b2) a mixture of at least one of the osmolality regulators mentioned under b1) in amounts of from 0.5 to 5% by weight and of polyethylene glycols, preferably polyethylene glycols having a molecular weight of from 1 000 to 8 000 g/mol, in amounts of from 10 to 20% by weight,
in each case based on the complete suspending medium including components a) and b1) or a) and b2).

The volume to be administered of the dosage forms of the invention which can be administered parenterally is preferably $\leq 5$ ml, particularly preferably $\leq 4$ ml and very particularly preferably $\leq 2$ ml.

The dosage forms of the invention which can be administered parenterally are preferably suitable for intramuscular or subcutaneous administration.

The amount of the active ingredient salt to be administered to the patient in the dosage forms of the invention may vary depending for example on the weight of the patient, and the nature or severity of the pain. The skilled worker is aware on the basis of the effect of analgesics what dosages of the active ingredient salt are to be employed to achieve the desired effect.

The dosage forms of the invention which can be administered parenterally can be produced by conventional methods known to the skilled worker.

The dosage forms of the invention are preferably produced on an aqueous basis by the method described below.

The excipients employed are dissolved in water for injections at room temperature or, where appropriate, with heating. In the case of liquid excipients, these are mixed with water. The solution or mixture obtained in this way is subsequently sterilized by filtration using a filter which retains microorganisms. The pore width of this filter is normally 0.2 µm. The filtration may, where appropriate, also take place before the addition of the excipients, but further production of the dosage forms should then take place under aseptic conditions.

The sterile salt of the active ingredients tramadol and diclofenac is subsequently suspended, preferably homogeneously, by stirring under aseptic conditions in the hydrophilic suspending medium obtained in this way, and the suspension obtained in this way is subsequently dispensed into suitable containers, preferably into vials.

Dosage forms of the invention on a hydrophobic basis are preferably produced by initially heat-sterilizing the hydrophobic suspending medium and, where appropriate, adding further excipients.

The sterile salt of the active ingredients tramadol and diclofenac is subsequently suspended, preferably homogeneously, by stirring under aseptic conditions in the hydrophobic suspending medium obtained in this way, and the suspension obtained in this way is subsequently dispensed into suitable containers, preferably into vials.

Where the production of the dosage forms of the invention which can be administered parenterally has not taken place under aseptic conditions, where appropriate a final sterilization can be carried out by conventional methods known to the skilled worker, for example by autoclaving. The suspensions of the invention which can be administered parenterally have preferably themselves been produced under aseptic conditions.

The dosage forms of the invention which can be administered parenterally are also distinguished inter alia by being stable, i.e. remaining suitable for administration, on storage over a prolonged period. No irreversible agglomeration occurs in the dosage forms of the invention even on storage for some months. It may in this connection be advantageous to put small inert solid bodies such as, for example, glass beads into the suspension vessel in order thus to achieve homogeneous resuspension more quickly again on shaking the stored suspension.

The dosage forms of the invention which can be administered parenterally have the further advantage that the analgesic active ingredient tramadol is available longer for controlling pain than with a parenteral tramadol hydrochloride drug form. This also makes effective control of pain possible even in patients for whom oral therapy using these active ingredients is unsuitable, without the need to administer tramadol for example more than twice a day to the patient. This achieves effective pain therapy with less stress for the patient. In addition, the delayed metabolism makes it possible to adjust constant serum levels of the active ingredient tramadol in the blood serum. It is possible in this way completely to avoid or at least markedly reduce high active ingredient concentrations like those frequently occurring with conventional dosage forms with rapid delivery of active ingredient, and the unwanted side effects associated therewith where appropriate.

FIG. 1 shows the time courses of the concentration of the (+)-tramadol enantiomer for the dosage forms of the invention and for a corresponding tramadol hydrochloride dosage form in the blood serum of dogs after parenteral administration.

FIG. 2 shows the time courses of the concentration of the (−)-tramadol enantiomer for the dosage forms of the invention and for a corresponding tramadol hydrochloride dosage form in the blood serum of dogs after parenteral administration.

PHARMACOLOGICAL INVESTIGATIONS 5 dogs (breed: beagle, breeder: Harlan-Winkelmann, Borchen, Germany) each received parenteral administration of the dosage form of the invention containing tramadol/diclofenac salt and of a corresponding tramadol hydrochloride dosage form. A blood sample was taken from each animal in each case at 0, 0.5, 1, 2, 4, 7, and for the dosage forms of the invention also at 24, hours after administration of the particular dosage form. A treatment-free period of at least 14 days was maintained between each administration of the dosage forms of the invention and between each tramadol hydrochloride dosage form.

After the blood samples were taken, they were centrifuged, the solid residue was discarded, and the blood serum obtained in this way was stored at a temperature below −20° C. until it was analyzed.

Each series of measurements consisted of in each case eight calibration samples differing in concentration, quality control samples with in each case two samples in three different concentration levels and the samples of unknown concentration to be analyzed. The corresponding calibration and quality control samples were made up in serum and processed together with the blood serum samples of unknown content.

The amounts of the tramadol enantiomers and, where appropriate, of the metabolites present in the blood serum at each time of measurement were concentrated using diazoethane as derivatizing reagent, and the samples obtained in this way were subsequently analyzed by stereoselective gas chromatography with nitrogen-selective detection.

The osmolality of the dosage forms of the invention was determined by freezing point depression as described in section 2.2.35 of Pharm. Eur. 97. The corresponding literature description is hereby introduced by reference and is thus regarded as part of the disclosure. The measurement took place using a type M measuring apparatus (Dr. H. Knauer KG, Berlin, Germany).

The calibration was carried out with distilled water for 0 mOsmol/kg and with a calibration solution (Dr. H. Knauer KG, Berlin, Germany) or alternatively 12.687 g of sodium chloride dissolved in 1 kg of distilled water for 400 mOsmol/kg.

The invention is explained by means of examples below. These explanations are merely by way of example and do not restrict the general concept of the invention.

EXAMPLES

Example 1

1st Stage: Preparation of the Active Ingredient Salt

To prepare the salt of the active ingredients tramadol and diclofenac, equimolar amounts of tramadol hydrochloride and diclofenac sodium were each dissolved completely under aseptic conditions in the minimum amount of water. The two solutions were then mixed together with stirring. The active ingredient salt crystallized after only a short time out of the aqueous solution on cooling and was isolated and purified with ethanol by conventional methods.

2nd Stage: Preparation of the Suspending Medium 0.03 g of polysorbate 80 Ph. Eur. (0.01% by weight), 3.00 g of sucrose Ph. Eur. (1.00% by weight) and 45.00 g of macrogol 4000 Ph. Eur. (15.00% by weight) were dissolved in 251.97 g of water for injections Ph. Eur. (83.99% by weight) in an autoclaved glass beaker by stirring at room temperature (20 to 25° C.). After all the solid starting materials had completely dissolved in water, the solution obtained in this way was filtered to remove impurities such as, for example, fibers or subvisible particles through a filter with a pore width of 5 µm (Millipore SVLP). The filtered solution was then autoclaved in a closed vessel at a temperature of 121° C. and a pressure of 2 bar for 30 minutes.

The osmolality of the solution obtained in this way was determined by the method indicated above and was 300 mOsm/kg.

3rd Stage: Production of the Dosage Form

The active ingredient salt obtained in the first stage was ground in a mortar under aseptic conditions so that 98% of the salt particles had a particle diameter of ≦30 µm. Subsequently, in each case 293.5 mg of the salt were suspended in 5 ml portions of the suspending medium obtained in the second stage and dispensed into a vial. For the resuspension which is necessary where appropriate, in each case 3 to 5 sterilized glass beads were also added, and the vials were each sealed with a sterilized bromobutyl rubber stopper and crimp-capped.

The dosage form obtained in this way was investigated by the method indicated above, and the respective concentrations of (+)-tramadol and (−)-tramadol in blood serum were determined. The result of these investigations for (+)-tramadol and the values for the corresponding tramadol hydrochloride dosage form are depicted in FIG. 1. The result for (−)-tramadol and the corresponding values of the tramadol hydrochloride dosage form are depicted in FIG. 2.

Example 2

1st Stage

Preparation of the Suspending Medium

To remove impurities such as, for example, fibers or subvisible particles, castor oil was filtered through a filter with a pore width of 5 µm (Millipore SVLP). The filtered oil was subsequently sterilized in a closed vessel at 150° C. for one hour.

2nd Stage

Production of the Dosage Form

The active ingredient salt prepared as in example 1, 1st stage, was ground in a mortar under aseptic conditions so that 98% of the salt particles had a particle diameter of ≦30 µm. Subsequently, in each case 293.5 mg of the salt were suspended in 5 ml of the hydrophobic suspending medium obtained in the first stage and dispensed into a vial. For the resuspension which is necessary where appropriate, in each case 3 to 5 sterilized glass beads were also added, the vials were sealed with sterilized bromobutyl rubber stoppers and subsequently crimp-capped.

The dosage form obtained in this way was investigated by the method indicated above, and the respective concentrations of (+)-tramadol and (−)-tramadol in blood serum were determined. The result of these investigations for (+)-tramadol and the values for the corresponding tramadol hydrochloride dosage form are depicted in FIG. 1. The result for (−)-tramadol and the corresponding values of the tramadol hydrochloride dosage form are depicted in FIG. 2.

What is claimed is:

1. A delayed metabolism dosage form of tramadol which can be administered parenterally, comprising a suspension of the salt which is a reaction product of the active ingredients tramadol and diclofenac.

2. A dosage form which can be administered parenterally as claimed in claim 1, characterized in that at least 95% of the suspended salt particles have a particle diameter in the range ≦50 µm, preferably in the range ≦30 µm, particularly preferably in the range ≦5 µm.

3. A dosage form which can be administered parenterally as claimed in claim 1, characterized in that the volume of the dosage form to be administered is ≦5 ml, preferably ≦4 ml, particularly preferably ≦2 ml.

4. A dosage form which can be administered parenterally as claimed in claim 1, characterized in that the suspending medium is a physiologically tolerated hydrophobic suspending medium.

5. A dosage form which can be administered parenterally as claimed in claim 4, characterized in that a synthetic, semisynthetic or natural oil or a mixture of at least two of the aforementioned oils is present as hydrophobic suspending medium.

6. A dosage form which can be administered parenterally as claimed in claim 5, characterized in that medium chain length triglycerides with a chain length of from $C_8$ to $C_{10}$ in the carboxylic acid moiety, soybean oil, sesame oil, peanut oil, olive oil, coconut oil, castor oil, sunflower oil, safflower oil or the corresponding hydrogenated oils or a mixture of at least two of the aforementioned compounds, preferably castor oil, where appropriate in combination with physiologically tolerated antioxidants, preferably tocopherols and/or tocopherol esters, butylated hydroxyanisole and/or butylated hydroxytoluene, is present as oil.

7. A dosage form which can be administered parenterally as claimed in claim 1, characterized in that the suspending medium is a physiologically tolerated hydrophilic suspending medium.

8. A dosage form which can be administered parenterally as claimed in claim 7, characterized in that the hydrophilic suspending medium is based on water.

9. A dosage form which can be administered parenterally as claimed in claim 1, characterized in that pH regulators, regulators for adjusting the osmolality, surface-active compounds, viscosity regulators, peptizers, buffers, preservatives or a mixture of at least two representatives of various aforementioned classes of regulators or of at least two representatives of one class of regulators are present as. further physiologically tolerated excipients.

10. A dosage form which can be administered parenterally as claimed in claim 9, characterized in that polyalkylene glycols, phospholipids, ethers or esters of saturated or unsaturated fatty alcohols or fatty acids with polyalkylene glycols, polysorbates or mixtures of at least two representatives of various aforementioned classes of compounds or of at least two representatives of one class of regulator are present as surface-active compounds.

11. A dosage form which can be administered parenterally as claimed in claim 10, characterized in that polyethylene glycols, polypropylene glycols ethylene oxide, propylene oxide block copolymers or mixtures of at least two of these polyalkylene glycols are present as polyalkylene glycols.

12. A dosage form which can be administered parenterally as claimed in claim 10, characterized in that ethers or esters of saturated or unsaturated fatty alcohols or fatty acids with polyethylene glycols and/or polypropylene glycols are present.

13. A dosage form which can be administered parenterally as claimed in claim 10, characterized in that mono-, di- or triesters of saturated or unsaturated fatty acids and sorbitol and/or its anhydride, each of which may have up to 20 mol of ethylene oxide units per mole of sorbitol or anhydride, or mixtures of at least two of these polysorbates are present as polysorbates.

14. A dosage form which can be administered parenterally as claimed in claim 13, characterized in that oleic acid, lauric acid, palmitic acid or stearic acid is present as fatty acid.

15. A dosage form which can be administered parenterally as claimed in claim 13, characterized in that polyethoxysorbitan monolaurate with 20 ethylene oxide units, polyethoxysorbitan monolaurate with 4 ethylene oxide units, polyethoxysorbitan monopalmitate with 20 ethylene oxide units, polyethoxysorbitan monostearate with 20 ethylene oxide units, polyethoxysorbitan monostearate with 4 ethylene oxide units, polyethoxysorbitan tristearate with 20 ethylene oxide units, polyethoxysorbitan monooleate with 20 ethylene oxide units, polyethoxysorbitan monooleate with 5 ethylene oxide units or polyethoxysorbitan trioleate with 20 ethylene oxide units, or a mixture of at learnt two of the aforementioned compounds, is present as polysorbate.

16. A dosage form which can be administered parenterally as claimed in claim 9, characterized in that water-soluble physiologically tolerated inorganic salts, sugars, sugar alcohols or polyalkylene glycols or mixtures of at least two representatives of different aforementioned classes of regulators or of at least two representatives of one class of regulators are present as regulators.

17. A dosage form which can be administered parenterally as claimed in claim 16, characterized in that the inorganic salt is an alkali metal salt, preferably sodium chloride.

18. A dosage form which can be administered parenterally as claimed in claim 16, characterized in that the sugar is sucrose and/or dextrose.

19. A dosage form which can be administered parenterally as claimed in claim 16, characterized in that the sugar alcohol is mannitol.

20. A dosage form which can be administered parenterally as claimed in claim 16, characterized in that the polyalkylene glycols are polyethylene glycols, preferably polyethylene glycols having a molecular weight of from 1 000 to 8 000 g/mol, particularly preferably polyethylene glycols having a molecular weight of from 2 500 to 5 000 g/mol.

21. A dosage form which can be administered parenterally as claimed in claim 9, characterized in that 1,1,1-trichloro-2-methyl-2-propanol, phenylethyl alcohol, sorbic acid, benzyl alcohol, alkylbenzyldimethylammonium chloride having a chain length of from $C_8$ to $C_{18}$ in the alkyl moiety, m-cresol, alkyl-4-hydroxybenzoate or a mixture of two or more of these aforementioned preservatives are present as preservatives.

22. A dosage form which can be administered parenterally as claimed in claim 21, characterized in that the alkyl -4-hydroxybenzoate is methyl -4-hydroxybenzoate and/or propyl -4-hydroxybenzoate.

23. A parenteral dosage form as claimed in claim 9, characterized in that the suspending medium is water which comprises
   a) 0,001 to 1% by weight, preferably 0.0015 to 0.1% by weight, particularly preferably 0.005 to 0.15% by weight of physiologically tolerated surface-active compounds, preferably polysorbates.
   b1) 3 to 10% by weight of at least one physiologically tolerated osmolality regulator selected from the group of mono-saccharides, oligosaccharides and sugar alcohols, or
   b2) a mixture of at least one of the osmolality regulators mentioned under b1) in amounts of from 0.5 to 5% by weight and of polyethylene glycols in amounts of from 10 to 20% by weight
in each case based on the complete suspending medium including components a) and b1) or a) and b2).

24. A dosage form which can be administered parenterally am claimed in claim 23, characterized in that sorbitol and/or its anhydride which is monoesterified with oleic acid, lauric acid, palmitic acid or stearic acid and etherified with polyethylene glycol, preferably with polyethylene glycol having a molecular weight of from 1 000 to 6 000 g/mol, particularly preferably from 2 500 to 5 000 g/mol, is present as polysorbates of component a).

25. A dosage form which can be administered parenterally as claimed in claim 23, characterized in that sucrose and/or mannitol is present as osmolality regulator of component b1).

26. A dosage form which can be administered parenterally as claimed in claim 23, characterized in that the polyethylene glycols of component b2) have a molecular weight of from 1 000 to 6 000 g/mol, preferably from 2 500 to 5 000 g/mol.

27. A dosage form which can be administered parenterally as claimed in claim 1 for subcutaneous or intramuscular administration.

28. The dosage form of claim 1 where the tramadol used is in the form of tramadol hydrochloride.

29. The dosage form of claim 1 where the diclofenac used is in the form of sodium diclofenac.

* * * * *